United States Patent [19]

Scandella et al.

[11] Patent Number: 5,149,637
[45] Date of Patent: Sep. 22, 1992

[54] RECOMBINANT FACTOR VIIIC FRAGMENTS

[75] Inventors: Dorothea H. Scandella, Gaithersburg, Md.; William N. Drohan, Springfield, Va.; Theodore S. Zimmerman; Carol A. Fulcher, both of LaJolla, Calif.

[73] Assignees: Scripps Clinic & Research Foundation, LaJolla, Calif.; Rorer Biotechnology Inc., Springfield, Va.

[21] Appl. No.: 585,766

[22] Filed: Sep. 20, 1990

Related U.S. Application Data

[62] Division of Ser. No. 34,828, Apr. 6, 1987, Pat. No. 4,980,456.

[51] Int. Cl.[5] ............ C12N 15/10; C12N 21/00; C07H 15/12; C07K 13/00
[52] U.S. Cl. ............ 435/69.6; 435/172.3; 435/320.1; 530/383; 530/350; 536/27
[58] Field of Search ............ 435/69.1, 69.2, 69.6, 435/172.1, 172.3, 320.1; 514/802; 530/383, 810; 536/27

[56] References Cited

U.S. PATENT DOCUMENTS

| 4,649,132 | 3/1987 | Zimmerman | 514/12 |
| 4,757,006 | 7/1988 | Toole | 435/70.21 |
| 4,980,456 | 12/1990 | Scandella | 530/383 |

*Primary Examiner*—Robert A. Wax
*Assistant Examiner*—Dian Cook
*Attorney, Agent, or Firm*—Rosanne Goodman; Martin F. Savitzky; James A. Nicholson

[57] ABSTRACT

New fragments of the Factor VIII procoagulant protein (Factor VIIIC) are disclosed. These fragments have an Mr value of 88,000 d or 49,000 d or extend from amino acid residues 1974 to 2332 or 2052 to 2332. These fragments have use in the treatment of patients who have developed antibodies which inhibit Factor VIII.

13 Claims, 6 Drawing Sheets

C4 MONOCLONAL ANTIBODY      C5 MONOCLONAL ANTIBODY 1    2        3    4

— 200 —

— 97 —

88kd →

— 68 —

← 49 kd

— 43 —

— 25 —

MOLECULAR WEIGHT (kd)

EXPRESSION INDUCED FROM:
1 pDS 1
2 pDS 3
3 pDS 1
4 pDS 3

RECOMBINANT FACTOR VIIIC FRAGMENTS

This is a divisional of copending application Ser. No. 07/034,828 filed on Apr. 6, 1987, now U.S. Pat. No. 4,980,456.

BACKGROUND OF THE INVENTION

1. Field of the Invention

This invention relates to fragments of the Factor VIII procoagulant protein (Factor VIIIC), their recombinant DNA-directed synthesis, and their potential use in the treatment of patients who have developed antibodies which inhibit Factor VIII.

2. Brief Description of the Prior Art

Normal human plasma contains a complex of two proteins which is referred to as the Factor VIII complex. One component of the Factor VIII complex has antihemophilic factor procoagulant activity and is designated Factor VIIIC. A deficiency in Factor VIIIC is characteristic of hemophilia A, a disease transmitted by X-chromosomal inheritance.

The conventional treatment for hemophilia A is administration of Factor VIIIC (antihemophilic factor, or "AHF"), concentrated in any of various means from the plasma of donors. Some hemophiliacs exhibit, in effect, "resistance" to this treatment, in that administration of Factor VIIIC in doses which are usually effective for most hemophiliacs produces reduced or no therapeutic effect.

This phenomenon has generally been considered to be due to one or more antibody inhibitors of Factor VIIIC in the circulatory system of the afflicted individual. (Persons who are not hemophiliacs can also develop these inhibitors.) It may be possible to treat Factor VIIIC inhibitors by administering greatly increased amounts of Factor VIIIC, some of which serve to saturate the inhibitory capacity of the Factor VIIIC inhibitor and the remainder of which provide the desired therapeutic effect uninhibited. However, this approach is extremely expensive, consumes large amounts of AHF per patient, and carries the risk of increasing the amounts of other products or agents, unavoidably present with the Factor VIIIC, to which the patient is exposed. Thus, there is a need for a product which effectively neutralizes the activity of Factor VIII inhibitors, without introducing unnecessary co-products.

In the bloodstream, the protease thrombin cleaves Factor VIIIC to yield fragments which are active in blood coagulation, and then it further cleaves some fragments into inactive species. These useful properties of thrombin can be employed in vitro to generate a series of unique subfragments of Factor VIIIC.

Recently, it has been shown by Fulcher et al., *Proc. Natl. Acad. Sci. USA*, 82:7728 (1985) that the patient inhibitor antibodies bind to only some of the Factor VIIIC fragments generated by thrombin cleavage, i.e., fragments of 44,000 d and 72,000 d. One option for removing inhibitor activity is thus to inject inhibitor patients only with the required Factor VIIIC fragments rather than the full-length molecule.

Genes coding for polypeptides such as Factor VIIIC or fragments of Factor VIIIC may be cloned by incorporating a DNA fragment encoding the polypeptide into a recombinant DNA vehicle (e.g., prokaryotic or eukaryotic vectors) and transforming a suitable host. Such recombinant DNA techniques have now become well known and are described in *Methods In Enzymology*, (Academic Press), Volumes 65 and 68 (1979), 100 and 101 (1983), and the references cited therein, which are incorporated herein by reference. An extensive technical discussion embodying most commonly used recombinant DNA methodologies can be found in Maniatis et al., *Molecular Cloning*, Cold Spring Harbor Laboratory (1982).

One way of obtaining a DNA fragment encoding a desired polypeptide such as Factor VIIIC is via cDNA cloning. In this process, messenger RNA (mRNA) is isolated from cells known or suspected of producing the desired protein. Through a series of enzymatic reactions, the mRNA population of the cells is copied into a complementary DNA (cDNA). The resulting cDNA is then inserted into cloning vehicles and subsequently used to transform a suitable prokaryotic or eukaryotic host. The resultant gene "library" is comprised of a population of transformed host cells, each of which contain a single gene or gene fragment. The entire library, therefore, provides a representative sample of the coding information present in the mRNA mixture used as a starting material.

Gene libraries are screened using specific nucleic acid or antibody probes. Nucleic acid probes are useful for locating cDNAs by hybridization and autoradiography techniques. This approach, however, requires previous knowledge of at least a portion of the protein's amino acid or DNA-encoding sequence. Alternatively, methods have been developed to identify specific clones by probing recombinant gene libraries with antibodies specific for the encoded protein of interest. This method can only be used with "expression vector" cloning vehicles since elaboration of the product protein is required. An example of this is the bacteriophage lambda gt11 system described by Young and Davis, *Proc. Natl. Acad. Sci. USA*, 80:1194–1198 (1983) and Young and Davis, *Science*, 22:778 (1983).

Once isolated, these cDNAs can be genetically engineered. Gene fragments can be assembled into complete genes. Alternatively, as described in this invention, specific fragments of a gene can be engineered independently of the rest of the gene. Protein fragments encoded by these engineered gene fragments may not be found in nature, yet they may have significant utility in treating undesirable physiological conditions. The engineering of recombinant Factor VIIIC fragments for treatment of anti-Factor VIIIC antibody producing hemophiliac or non-hemophiliac patients is one such case.

SUMMARY OF THE INVENTION

The present invention relates to recombinant Factor VIIIC fragments. The fragments have been achieved by the application of recombinant DNA technology to prepare cloning vehicles encoding the Factor VIIIC sequence and inserting parts of this sequence into vehicles containing the appropriate regulatory signals for gene expression in the bacterium *Escherichia coli* (*E. coli*) or in eukaryotic cells and by use of appropriate procedures for recovering Factor VIIIC fragments essentially free of other proteins of bacterial origin. These fragments can be used in the treatment of the blood coagulation disorders of inhibitor patients.

The invention provides replicating expression vectors incorporating a DNA sequence encoding Factor VIIIC fragments and a self-propagating host cell system transformed thereby. The host system is either prokaryotic, e.g., *E. coli* or eukaryotic cells.

The recombinant Factor VIIIC fragments are produced by a process which comprises (a) preparing a replicable expression vector capable of expressing the DNA sequence encoding a Factor VIIIC fragment in a suitable host cell system; (b) transforming said host system to obtain a recombinant host system; (c) maintaining said recombinant host system under conditions permitting expression of said Factor VIIIC fragment-encoding DNA sequence to produce Factor VIIIC fragment protein; and (d) recovering said Factor VIIIC fragment protein. Preferably, the fragment-encoding replicable expression vector is made by preparing a ds-cDNA preparation representative of Factor VIIIC mRNAs and incorporating the ds-cDNA into replicable vectors. Fragments of the gene are then placed downstream from specific DNA sequences mediating gene expression in the host. The preferred mode of recovering Factor VIIIC fragments comprises reacting the proteins expressed by the recombinant host system with a reagent composition comprising at least one binding step specific for the Factor VIIIC fragment.

DESCRIPTION OF THE INVENTION

A. Introduction

Figure 1:
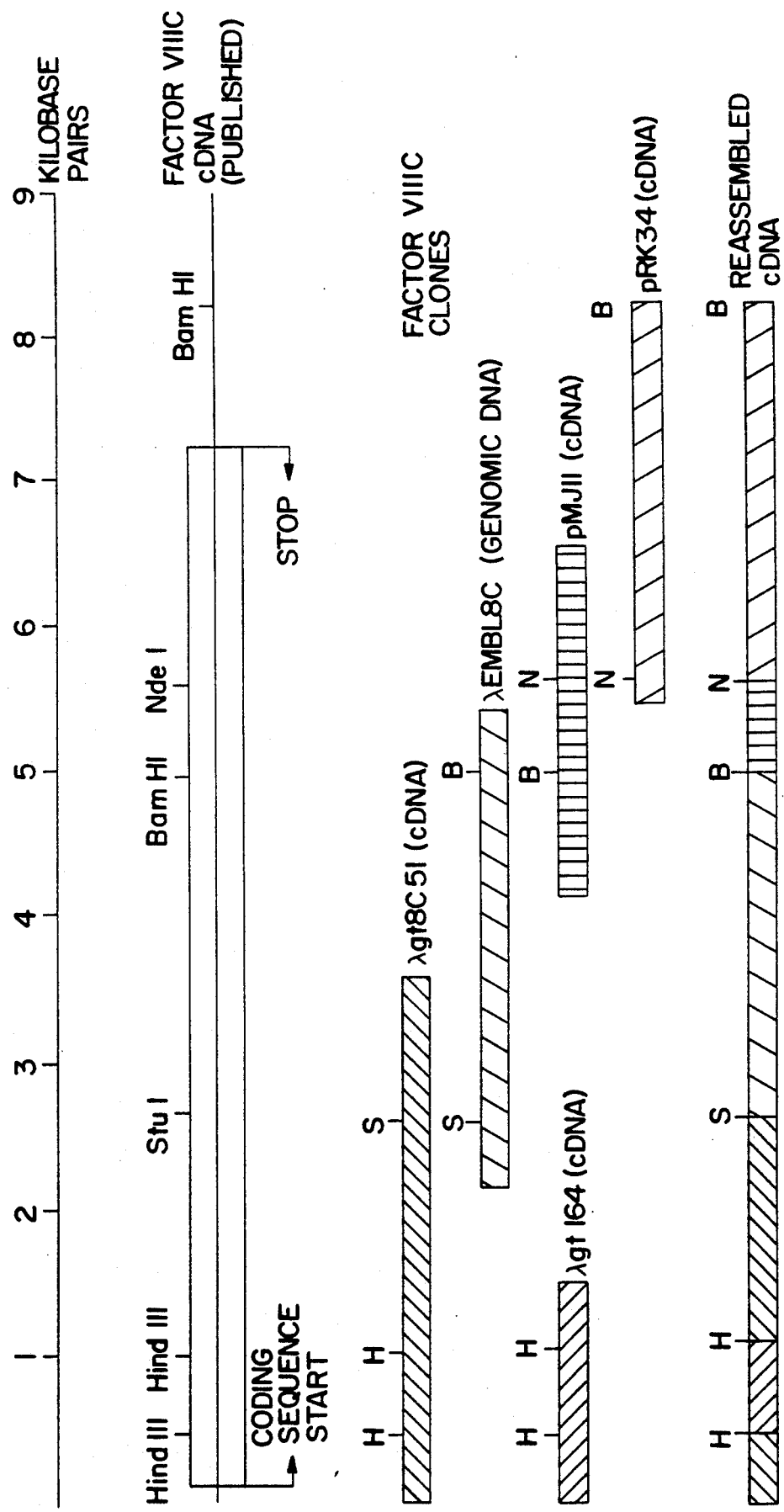
FIG. 1 diagrams the assembly of the full-length Factor VIIIC cDNA sequence.

As used herein, "Factor VIIIC fragment" denotes fragments of human Factor VIIIC which are produced in in vitro cell culture systems, in bioactive forms having the capacity to bind inhibitor antibodies as does Factor VIIIC native to human plasma.

Analogs of Factor VIIIC fragments may exist in nature. These variations may be characterized by differences in the nucleotide sequence of the structural gene coding for proteins of identical biological function. It is also possible to engineer fragments having single or multiple amino acid substitutions, deletions, additions or replacements. All such variants (naturally derived, synthetic, or genetically engineered) resulting in derivatives of Factor VIIIC which retain the inhibitor binding properties of native Factor VIIIC are included within the scope of this invention. The fragment may be recombinant-derived protein identical to fragments identified in cDNA libraries or newly engineered fragments with no counterparts in vivo.

"Inhibitors" refer to antibodies produced by individuals who have undergone multiple transfusion therapies with Factor VIIIC concentrates. The inhibitors can also be acquired spontaneously in subjects with previously normal hemostatis and without prior exposure to Factor VIIIC containing blood products. The inhibitor antibodies inactivate Factor VIIIC normally present in human plasma or Factor VIIIC transfused into a patient with a clotting factor deficiency.

"Expression vectors" refer to vectors which are capable of replicating and transcribing DNA sequences contained therein, where such sequences are linked to other regulatory sequences capable of affecting their expression. These expression vectors must be propagated in the host organisms or systems either as autonomous episomes or as an integral part of the chromosomal DNA.

One form of expression vector which is suitable for use in the invention is the bacteriophage, a virus which replicates in bacteria. The lambda gt11 phage is particularly desirable for this purpose. Lambda gt11 is a general recombinant DNA expression vector capable of producing polypeptides specified by the inserted DNA. To minimize degradation, upon induction with a synthetic analog of lactose (IPTG), foreign proteins or portions thereof are synthesized as fused proteins with the prokaryotic protein beta-galactosidase. The use of host cells defective in protein degradation pathways may also increase the longevity of novel proteins produced from the induced lambda gt11 clones. Proper expression of foreign DNA in lambda gt11 clones will depend upon the proper orientation and reading frame of the inserted DNA with respect to the beta-galactosidase gene. Another form of expression vector useful in recombinant DNA techniques is the prokaryotic plasmid: an unintegrated (extrachromosomal), double-stranded DNA circle. A third class of expression vectors are the eukaryotic vectors: vectors capable of driving expression of the foreign DNA in a eukaryotic cell. These are generally derived from viral sources and may be either extrachromosomal or integrated. The invention includes any other form of expression vector which serves an equivalent function and which is or subsequently becomes known in the art.

Recombinant vectors and methodology disclosed herein are suitable for use in a wide range of prokaryotic and eukaryotic host cells. These host cells include microbial stains, such as *E. coli* K12, *Saccharomyces cerevisiae*, and cell lines derived from multicellular eukaryotic organisms.

"Recombinant host cells" refer to cells which have been transformed with vectors constructed using recombinant DNA techniques. As defined herein, Factor VIIIC fragments are produced as a consequence of this transformation. Factor VIIIC fragments or subunits thereof produced by such cells are referred to as "recombinant Factor VIIIC fragments".

B. Recombinant and Screening Methodology

The procedures below are but some of a wide variety of well-established procedures to produce specific reagents useful in the process of this invention. The general procedure for obtaining an mRNA mixture is to obtain a tissue sample or to culture cells producing the desired protein, and to extract the RNA by a process such as that published by Chirgwin et al., *Biochemistry*, 18:5294 (1979). The mRNA is isolated by enriching for poly(A)-containing RNA by chromatography of the RNA on oligo (dT) cellulose or poly(U) Sepharose.

The above poly(A) containing mRNA-enriched fraction is used to synthesize a single-strand complementary cDNA (ss-cDNA) using reverse transcriptase. As a consequence of DNA synthesis, a hairpin loop is formed at the 3' end of the DNA which will initiate second-strand DNA synthesis. Under appropriate conditions, this hairpin loop is used to initiate synthesis of the ds-cDNA in the presence of DNA polymerase and nucleoside triphosphates.

The resultant ds-cDNA is inserted into a vector by any one of many known techniques. In general, the vector is linearized by at least one restriction endonuclease, which will produce at least two blunt or cohesive ends. The ds-cDNA is ligated with (or joined into) the vector insertion site.

Prokaryotic cells are made competent by calcium chloride pretreatment and transformed with the DNA. After isolating the successfully engineered cells, the cells are cultured on selective media, and proteins encoded by the expression vector are produced.

Clones containing part or the entire cDNA for Factor VIIIC fragments are identified with specific antibodies directed against part or all of the Factor VIIIC fragment protein. This method of identification requires that the ds-cDNA be inserted into a vector containing appropriate regulatory nucleic acid sequences adjacent to the insertion site. These regulatory sequences initiate transcription and translation of those ds-cDNA molecules inserted in the vector. Those clones containing Factor VIIIC fragment cDNA sequences correctly positioned relative to the regulatory sequences, synthesize part or all of the Factor VIIIC fragment protein. Such clones are detected using appropriately specific antibodies. Such a cloning system is the lambda gt11 system.

Clones containing the remaining sequence of Factor VIIIC are identified using as probe the cDNA insert of the Factor VIIIC fragment recombinants isolated during the initial screening of the recombinant lambda gt11 cDNA library. Nucleotide sequencing techniques are used to determine the sequence of amino acids encoded by the cDNA fragments. This information may be used to determine the identity of cDNA clones as specific for human Factor VIIIC fragments by comparison to the known amino acid sequence of Factor VIIIC. Alternatively, identification may be confirmed by employing techniques such as hybrid-selected translation or by comparison to Factor VIIIC clones isolated from other species, e.g., mouse, rat, etc. The identified clones can ultimately be joined to form the sequence encoding the entire Factor VIIIC protein molecule.

EXAMPLE

A. Preparation of Total RNA

Total RNA was extracted from fresh frozen normal adult liver. Cells were homogenized in 15 volumes of a solution containing 4 M guanidine thiocyanate, 25 mM sodium citrate at pH 7.0, 0.5% N-laurylsarcosine, 0.1 M 2-mercaptoethanol, and 0.2% Antifoam A. The homogenate was centrifuged at 6,000 xg for 15 minutes at 10° C. The supernatant fluid was adjusted to pH 5.0 by addition of acetic acid, and the RNA was precipitated by 0.75 volumes of ethanol at −20° C. overnight. RNA was collected by centrifugation and dissolved in 7.5 M guanidine hydrochloride containing 25 mM sodium citrate and 5mM dithiothreitol. Following two additional precipitations using 0.5 volumes of ethanol, the residual guanidine hydrochloride was extracted from the precipitate with absolute ethanol. RNA was dissolved in sterile water, insoluble material removed by centrifugation, and the pellets were re-extracted with water. The RNA was adjusted to 0.2 M potassium acetate and precipitated by addition of 2.5 volumes of ethanol at −20° C. overnight.

B. Preparation of Poly(A)-Containing RNA

The total RNA precipitate, prepared as described above, was dissolved at a concentration of 40 $A_{260}$ units per ml in 20 mM Hepes buffer at pH 7.2 containing 10 mM EDTA and 1% SDS, heated at 65° C. for 10 minutes, and then quickly cooled to 25° C. The RNA solution was then diluted with an equal volume of water, and NaCl was added to bring the final concentration to 300 mM NaCl. Samples containing up to 2400 $A_{260}$ units of RNA were chromatographed on poly-(u)-sepharose using standard procedures. Poly(A)-containing RNA was eluted with 90% formamide containing 1 mM Hepes buffer (pH 7.2) and 2 mM EDTA. The eluate was adjusted to 0.24 M NaCl, and the RNA was precipitated with the addition of 2.5 volumes of ethanol at −20° C.

C. Construction of cDNA Clones in Lambda gt11

All enzymatic reactions were carried out using essentially standard techniques. The mRNA (20 ug) was copied into ds-cDNA with reverse transcriptase and DNA polymerase I. The ds-cDNA was desalted on Sephadex G-50, and the void-volume fractions further purified on a Elutip-d column (Schleicher & Schuell, Keene, NH) following the manufacturer's directions. The ds-cDNA was made blunt-ended by incubation with S1 nuclease. The reaction mixture consisted of 0.2 M sodium acetate (pH 4.5), 0.4 sodium chloride, 2.5 mM zinc acetate and 0.1 unit of S1 nuclease per ng of ds-cDNA, made to a final reaction volume of 100 ul. The ds-cDNA was incubated at 37° C. for one hour, extracted with phenol:chloroform, then desalted on a Sephadex G-50 column and Elutip purified as described above.

The ds-cDNA was then treated with EcoRI methylase and DNA polymerase I using reaction conditions described in Maniatis (supra). The cDNA was again desalted on Sephadex G-50, Elutip purified as described above and ligated to 0.5 ug of phosphorylated EcoRI linkers with T4 DNA ligase. The mixture was then cleaved with EcoRI and fractionated on an 8% acrylamide gel in Tris-Borate buffer. DNA with a size greater than 1 kilobase was eluted from the gel in 10 mM Tris (pH 7.5), 0.2 M NaCl and recovered by binding to an Elutip-d column, eluted with 1 M NaCl and then collected by ethanol precipitation.

The ds-cDNA was then inserted into EcoRI cleaved and phosphatase-treated lambda gt11 with T4 DNA ligase to produce a library of approximately twelve (12) million phage of which 50% contain inserts (i.e., six million clear plaques on X-gal plates). The library was amplified by producing plate stocks at 42° C. on E. coli Y1088 [supE supF metB trpR hsdR− hsdM+ tonA21 strA lacU169 proC::Tn5 (pMC9)]. Amplification procedures are described in Maniatis et al., (supra). The titer of the amplified library was determined to be $8 \times 10^{10}$ pfu/ml. Albumin cDNA clones represent 3–5% of the clear plaques in the library as judged by hybridization with a nick-translated albumin cDNA clone.

D. Identification of Clones Containing Factor VIIIC Sequence

To screen the library for Factor VIIIC antigenic determinant-producing clones, $1.1 \times 10^7$ lambda gt11 recombinant phage were plated (70,000 pfu/plate, 160 plates) on a lawn of E. coli Y1090 [lacU169 proA+ araD139 strA supF (trpC22::Tn10) (pMC9)] and incubated at 42° C. for 3 hours. This host is deficient in the lon protease, thereby reducing the degradation of expressed foreign protein. Nitrocellulose filters, previously saturated with 10 mM isopropyl thio-B-d-galactopyranoside (IPTG) and dried, were overlaid on the plates. The plates were then incubated at 37° C. overnight. Since IPTG is an inducer of lacZ transcription, the expression of foreign DNA inserts in lambda gt11 is under common control with lacZ transcription and, as such, is also induced. The position of the filters were marked with a needle, the filters removed, washed in TBS buffer (20 mM Tris, pH 7.5, and 500 mM NaCl) and incubated in TBS plus 3% gelatin for 30 minutes at room temperature.

The filters were then incubated at room temperature overnight in a 1:100 dilution of an emu polyclonal antibody [Fulcher and Zimmerman, *Proc. Natl. Acad. Sci. USA*, 79:1648 (1984)]) directed against Factor VIIIC in a buffer consisting of 1% gelatin in TBS. After 2 thirty-minute washes with TBS at room temperature, the filters were then incubated with a 1:200 dilution of rabbit anti-emu IgG. After 2 additional 30 minute washes with TBS, the filters were incubated with a 1:2,000 dilution of horseradish peroxidase (HRP) conjugated goat anti-rabbit antisera (Bio-Rad, Richmond, CA). The filters were then incubated 2 hours at room temperature in HRP color development solution as described in the Bio-Rad accompanying literature. Twenty-six putative positive plaques were identified.

A 4 mm-diameter plug at the position of the color development signal was removed from the plates and incubated in 10 mM Tris HCl, pH 7.5, and 10 mM MgSO$_4$ overnight. Approximately 10$^3$ plaque-forming units (PFU) were replated on 90 mm plates and re-screened as described above. Five clones remained positive through the second cycle of screening. This replating and rescreening process was repeated until all plaques on the plate produced a signal.

Phage DNA was isolated from each of the 5 clones. Restriction endonuclease cleavage analysis indicated that the 5 clones were identical and probably resulted as an artifact of the amplification procedure.

The cDNA insert from one of the clones was excised using a combination of the restriction enzymes EcoRI and PvuI. The EcoRI site to the right of the cloned cDNA was unexpectedly missing in all 5 clones; thus PvuI, which cuts at position 20.66 Kb in lambda gt11, was used in combination with EcoRI. The cDNA insert (approximately 1.2 Kb in length) was subcloned between the PvuI and EcoRI sites of pSP64 and subsequently used as a probe to rescreen the lambda gt11 library and human placental genomic library constructed in bacteriophage EMBL3.

A series of overlapping clones extending to the 5' and 3' direction of the original antibody positive clone, and encompassing full-length Factor VIIIC, were thus identified. The complete set of overlapping clones was sequenced and then assembled into a full-length cDNA clone as indicated diagrammatically in FIG. 1. The DNA sequence of the full-length Factor VIIIC coding region assembled at Meloy Laboratories, Inc., corresponds to nucleotides 1 through 7057 of Wood et al, *Nature*, 312:330-337 (1980). A clone containing this sequence in the expression vector described below has been deposited with the American Type Culture Collection (ATCC). Our designation of this clone is pdBPV/F8C-140-complete (p209.1). The ATCC patent deposit number for this clone is 53427, deposited on Jan. 20, 1986.

E. Construction of the Expression Vectors

Figure 2:
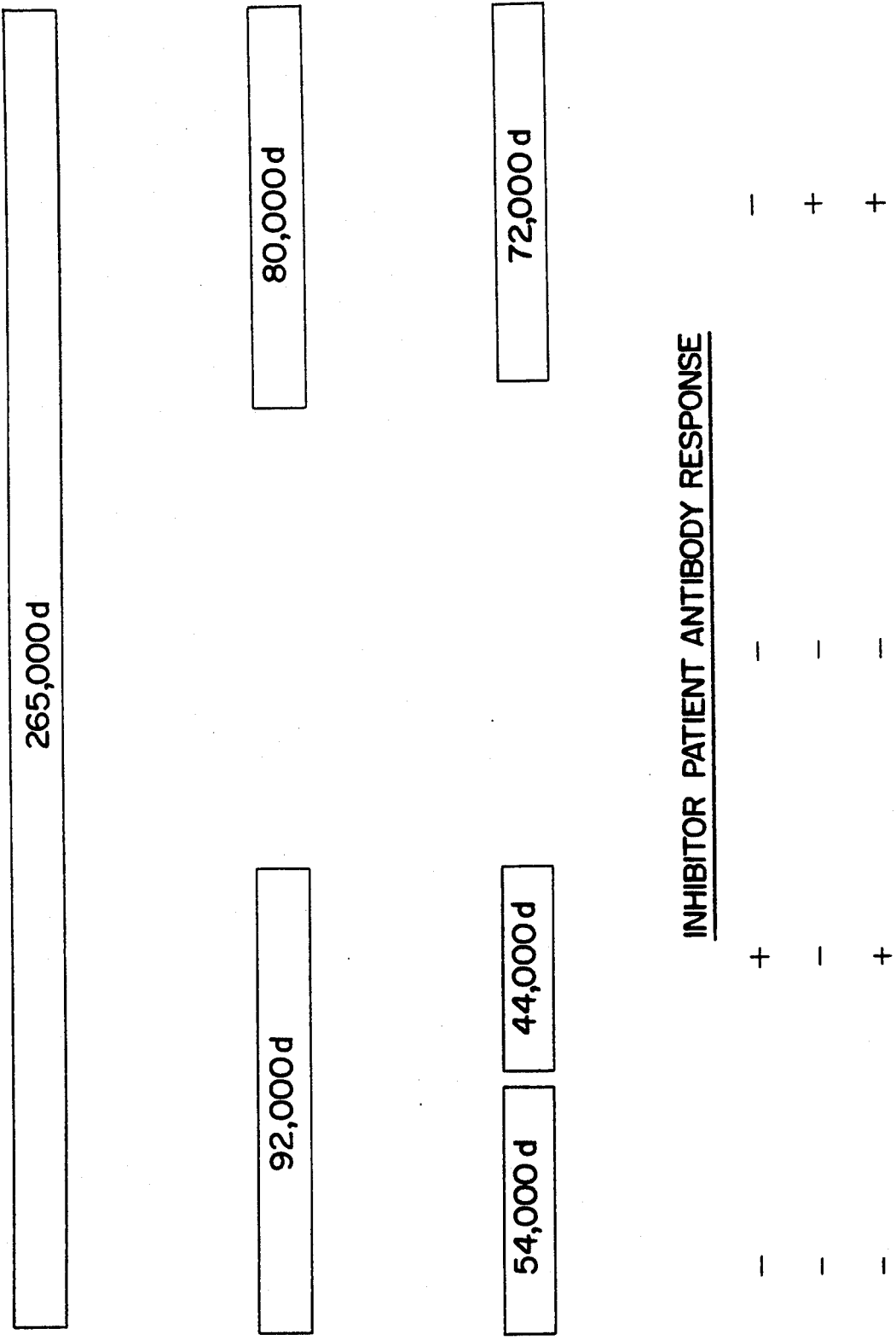
FIG. 2 illustrates the fragments generated by thrombin cleavage of Factor VIIIC. The heterogeneous fragments from the central region are not shown.

The diagram in FIG. 2 indicates the thrombin fragments of human Factor VIIIC which react with antibodies from inhibitor patients. Fragments from the central region are heterogeneous and are not specifically shown.

Figure 3:
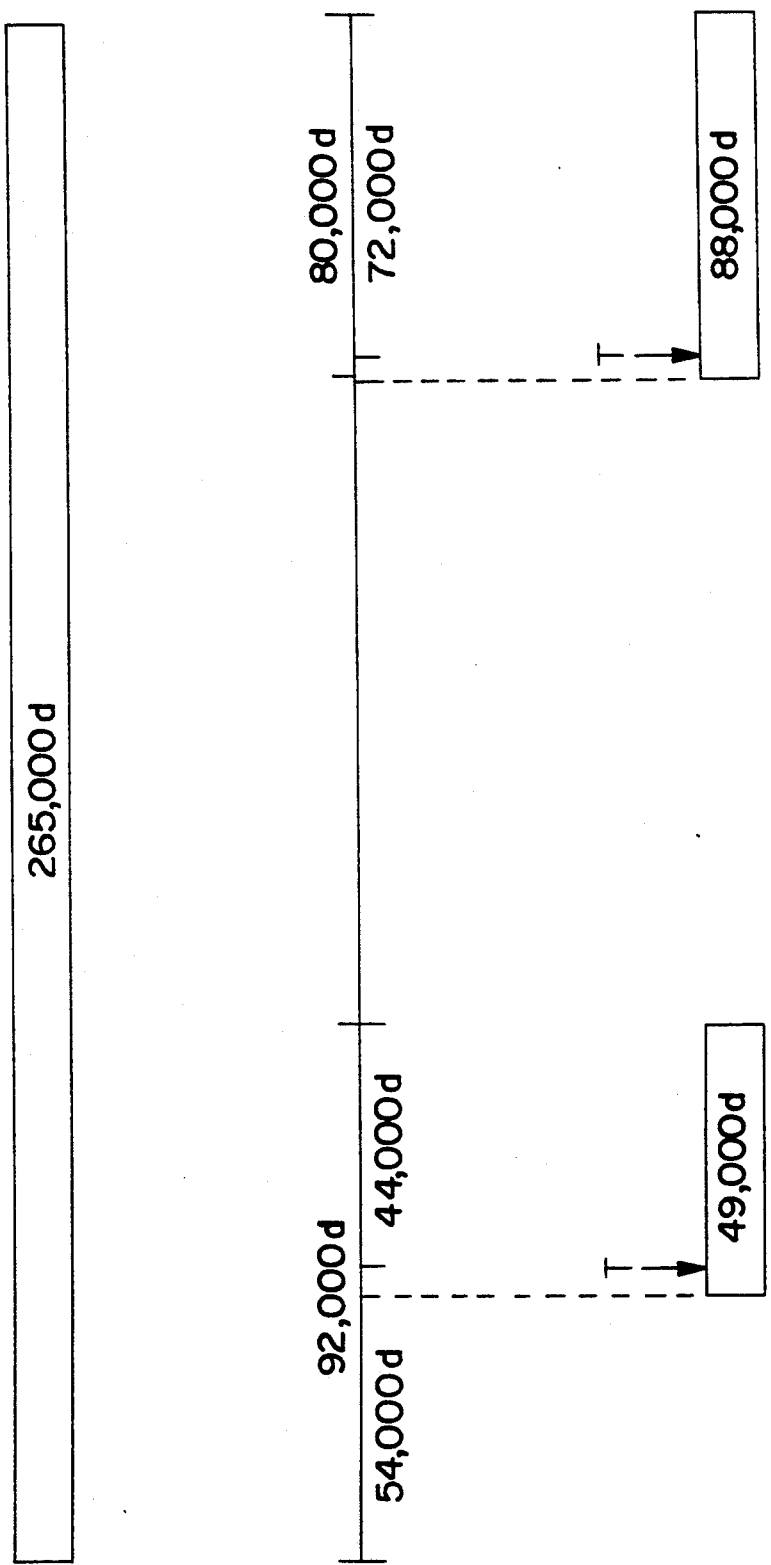
FIG. 3 illustrates the location on the Factor VIIIC cDNA sequence of fragments expressed in *E. coli*.

In the present invention recombinant fragments of 88,000 d and 49,000 d have been produced because the larger fragments contain an internal thrombin cleavage site (FIG. 3). By using thrombin to digest the larger fragments, one can generate polypeptides having the same amino terminal amino acid residues as fragments isolated from human Factor VIIIC and generated in the bloodstream during coagulation.

Pre-expression vectors containing the appropriate Factor VIIIC fragments were constructed from the cDNA clones using naturally occurring restriction cleavage sites. The plasmid pF8H3 was constructed to contain a HindIII DNA fragment (base pairs 1021-2278, numbering of Wood et al., *Nature*, 312:330, 1984) which encodes in part the 44,000 d thrombin-generated protein fragment. Plasmid p8C34MJ was similarly constructed to contain a BamHI DNA fragment (base pairs 4744-8231, Wood et al., supra), encoding in part the 77,000 d thrombin-generated protein fragment. The structure of each plasmid is shown in FIGS. 4 and 5.

The plasmid pCQV2 (Queen, *J. Mol. and Appl. Genet.*, 2:1, 1983) was used to provide a strong promoter, P$_R$ from bacteriophage lambda, a ribosome binding site, and an ATG for translation initiation. The ATG overlapped a BamHI restriction site (GGATCC) as follows: ATGGATCC. pCQV2 also contains the phage lambda cI857 temperature sensitive repressor which blocks transcription from P$_R$ at 30° C. but not at 42° C. Expression of a gene placed 3' to P$_R$ in this vector can thus be induced by shifting the temperature from 30° C. to 42° C.

Figure 4:
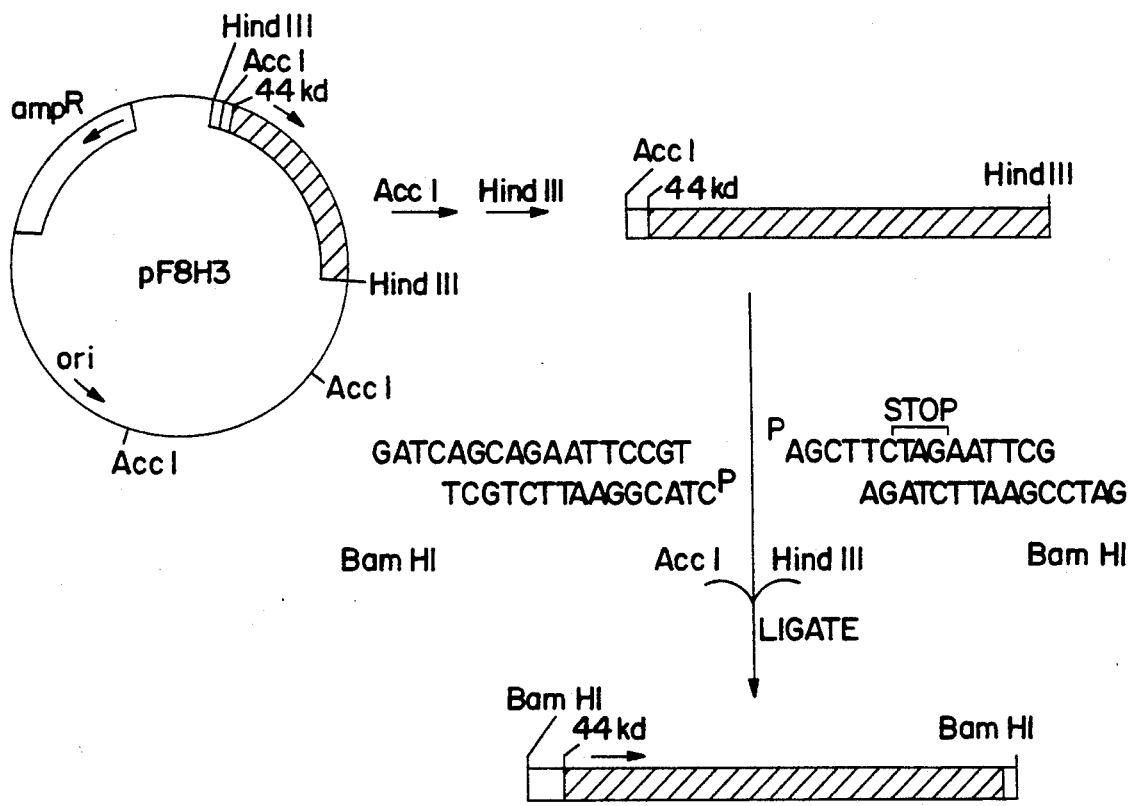
FIG. 4 illustrates the method of constructing an *E. coli* expression vector for the 49 kd gene fragment.
Figure 4:
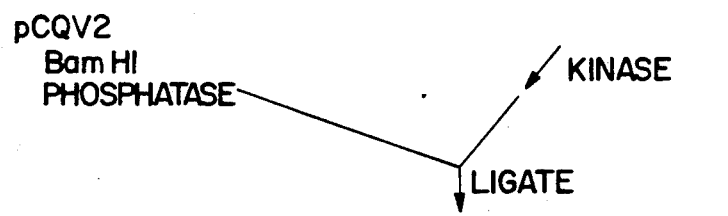
Figure 4:
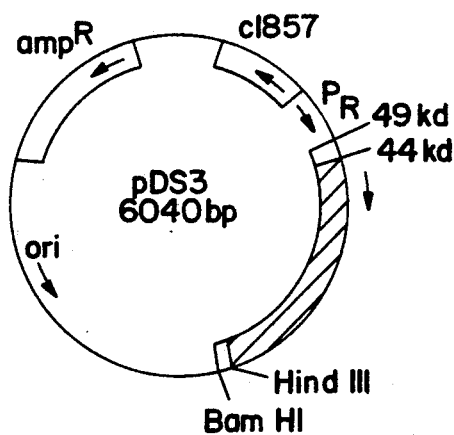
Figure 5:
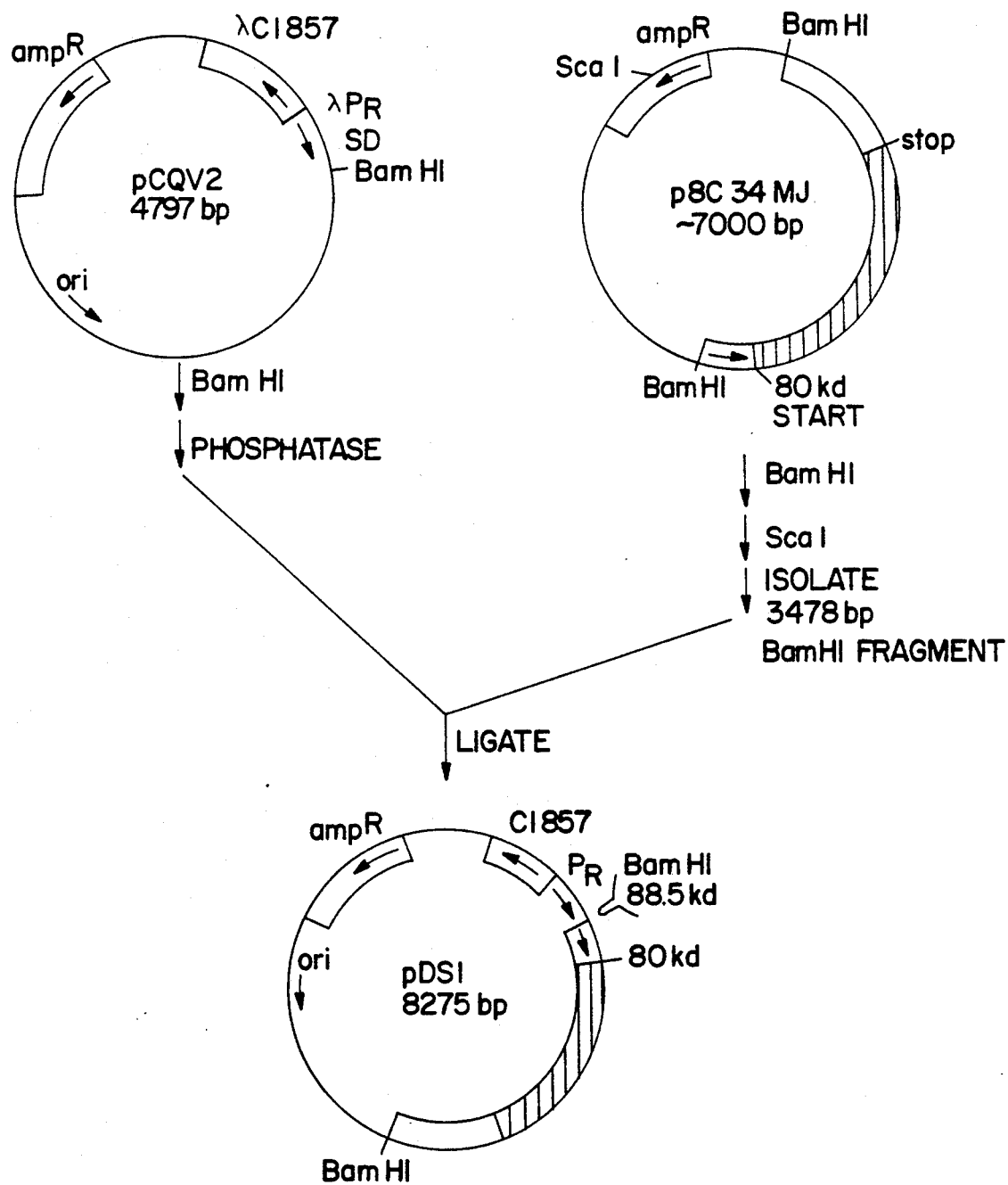
FIG. 5 illustrates the method of constructing an *E. coli* expression vector for the 88 kd gene fragment.

The strategy for cloning the DNA fragment encoding the 49,000 d protein into pCQV2 is shown in FIG. 4. All enzymes were used as suggested by the manufacturer.

pCQV2 (3 ug) was digested with 10 units of BamHI [Bethesda Research Labs, (BRL)]for 2 hours at 37° C. and treated with 2.2 units of calf alkaline phosphatase (Boehringer Mannheim) for 45 minutes at 37° C. The digested DNA was extracted with phenol and precipitated with ethanol. pF8H3 (50 ug) was digested with AccI (New England BioLabs) twice for 18 hours at 37° C. and with HindIII (New England BioLabs) for 3 hours at 37° C. The DNA was extracted with phenol and precipitated with ethanol. Oligonucleotide linkers were added to each end as shown in FIG. 4. One member of each pair (see Figure) was phosphorylated in a reaction containing 5 ug oligonucleotide, 2 units T4 polynucleotide kinase (Boehringer Mannheim), and 40 uCi $^{32}$P-ATP for 15 minutes at 37° C. A further 2 units kinase and ATP to 1 mM were added, and incubation was continued for 5 minutes. After phenol and chloroform extraction, each oligonucleotide was added to 5 ug of the oligonucleotide complementary to it, heated at 65° C. for 5 minutes, and allowed to anneal at 23° C. for 2 hours. The two pairs of oligonucleotides were ligated to 7.5 ug pF8H3 (AccI, Hind III) with 800 units T4 ligase (New England BioLabs) for 18 hours at 15° C.

The appropriate DNA fragment was isolated after electrophoresis on an 0.8% agarose gel by freezing the gel slice repeatedly in the presence of phenol and then separating the aqueous phase by centrifugation. The DNA in the aqueous phase was precipitated by ethanol. The ends of the isolated fragment+oligonucleotide linkers were phosphorylated as above and then ligated to 0.3 ug pCQV2 at 15° C. for 18 hours. Half of the ligation mixture was used to transform *E. coli* K12 JM101 (Yanisch-Perron et al., *Gene*, 33:103, 1985) made competent by CaCl₂ treatment and plated on LB agar +100 ug/ml ampicillin at 30° C. The correct orientation of the Factor VIIIC segment relative to $P_R$ was determined by restriction analysis of plasmid DNA isolated from transformant colonies.

The expression vector encoding the 88,000 d protein fragment was constructed as shown in FIG. 5. The convenient placement of two BamHI restriction sites, one 258 base pairs 5' to the 80,000 d start and the other in the 3' untranslated DNA, made the isolation of this DNA fragment and its insertion site pCQV2 (BamHI digested as above) simple; however, the protein encoded by this segment would contain additional amino acid residues at the amino terminal end, resulting in a protein of 88,000 d. This extra region can be removed by thrombin cleavage to generate a 72,000 d protein.

p8C34MJ (3 ug) was digested with BamHI (BRL) and ScaI (New England BioLabs). Since p8C34 yields two BamHI fragments of equal size, ScaI digestion was used to further cleave the fragment which contains only the vector sequences. The Factor VIIIC fragment in p8C34MJ contains no ScaI site, and it can then be easily purified away from the vector fragments. The Factor VIIIC 3478 bp BamHI fragment was isolated from the vector fragments. The Factor VIIIC 3478 bp BamHI fragment was isolated from an agarose gel as above. The fragment (0.3 ug) was ligated to 0.3 ug of the pCQV2 vector prepared above in the presence of three units of T4 DNA ligase (Boehringer Mannheim) at 15° C. for 4.5 hours. Half the ligation reaction was used to transform 200 ul competent *E. coli* K12 JM105 (Yanisch-Perron et al., supra) prepared by CaCl₂ treatment and plated on LB agar+10 ug/ml ampicillin at 30° C. The correct orientation of the Factor VIIIC fragment was determined by restriction analysis of plasmid DNA isolated from transformant colonies.

F. Expression of Factor VIIIC Fragments

Figure 6:
FIG. 6 illustrates the expression of 49 kd and 88 kd proteins in *E. coli* by Western blot analysis.

Plasmid DNA of pDS1 or pDS3 was used to transform competent *E. coli* K12 LC137 lac$_{am}$ trp$_{am}$ pho$_{am}$ rpsL supC$_{ts}$ mal$_{am}$ tsx::Tn10 htpR165$_{am}$ lonR9. Cultures of the transformed cells were grown in LB medium+100 ug/ml ampicillin at 30° C. until they reached A595 of 0.4. The cells were pelleted by centrifugation and suspended in 0.1 volume sample buffer and boiled 10 minutes. Aliquots of 40 ug protein were subjected to electrophoresis on 10% polyacrylamide-SDS gels and electroblotted onto nitrocellulose paper. Procedure for electroblotting and reaction with antibodies were performed following procedures supplied by BioRad, Inc. The primary antibodies [Fulcher et al., *J. Clin. Invest.* 76:117 (1985)]were mouse monoclonal antibodies specific for either the 54,000 d or 80,000 d thrombin fragments. The C4 monoclonal antibody, specific for the 80,000 d fragment, was diluted 1:50; and the C5 monoclonal antibody, specific for the 54,000 d thrombin fragment, was diluted 1:100. The epitope for C5 is located at the carboxyl terminus of the 54,000 d thrombin fragment which overlaps the beginning of the 49,000 fragment. The antibodies were incubated with nitrocellulose paper 15 hours at 23° C. The secondary antibody was affinity purified goat anti-mouse conjugated to alkaline phosphate (Promega Biotech) and incubated with the filter for 1 hours at 23° C. at a 1:7500 dilution. A color development reagent, obtained from Promega Biotech (nitro blue tetrazolium and 5-bromo-4-chloro-3-indolyl phosphate) and used according to their instructions, was used to visualize the Factor VIIIC protein bands shown in FIG. 6. Both full-length 49,000 d and 88,000 d bands could be seen.

The mouse monoclonal antibodies used in the Western blot assay were made using native human Factor VIIIC, and they react with subfragments of Factor VIIIC. The genetically engineered fragments produced in *E. coli* crossreact with the same antibodies; therefore, they are shown to be authentic Factor VIIIC fragments.

Following purification by standard procedures, the 49,000 d and 88,000 d proteins could be treated with thrombin to generate the 44,000 d and 72,000 d fragments for use in the treatment of inhibitor patients.

Deposit of Strains Useful in Practicing the Invention

A deposit of biologically pure cultures of the following strains was made with the American Type Culture Collection, 12301 Parklawn Drive, Rockville, Md., the accession number indicated was assigned after successful viability testing, and the requisite fees were paid. Access to said culture will be available during pendency of the patent application to one determined by the Commissioner to be entitled thereto under 37 C.F.R. Section 1.14 and 35 U.S.C. Section 122. All restriction on availability of said culture to the public(c will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

| Strain/Plasmid | ATCC No. | Deposit Date |
| --- | --- | --- |
| (A) 88,000 d protein *Escherichia coli* K12, JM105 (pDS1) | 67090 | April 16, 1986 |
| (B) 49,000 d protein *Escherichia coli* K12, JM101 (pDS3) | 67091 | April 16, 1986 |

Similar immunoblotting studies using human inhibitor plasmas showed that 7 hemophilia A inhibitors and 5 spontaneous inhibitors reacted with their corresponding bacterially producted Factor VIII fragments. Normal plasma or hemophilia A plasma without inhibitor did not react with these fragments.

Three deletions of the 88,000 fragment were constructed: amino acid residues 1571-1822, or 1829-2045, or 2052-2332 were deleted. Immunoblot analysis showed that the epitope(s) were present in deletion variants 1571-1822 and 1829-2045, but not in 2052-2332. Thus, a Factor VIII inhibitor epitope is present in that portion of Factor VIII extending from amino acid residues 2052 to 2332.

An expression vector encoding only amino acid resiudes 1974–2332 (37,500d) was then constructed. Partially purified 37,500 d fragment was able to neutralize the anti-Factor VIII activity of a hemophilic inhibitor against the 72,000 d thrombin fragment of Factor VIII in a standard Bethesda assay. As a control, a hemophilic inhibitor against the 44,000 d thrombin fragment of Factor VIII was not neutralized by this 37,500 d fragment. However, this inhibitor was neutralized by the 49,000 d bacterially expressed fragment. Thus, bacterially produced Factor VIII fragments reacted with inhibitors after immunoblotting and neutralized inhibitor activity in vitro.

Such recombinant Factor VIII fragments can be used by themselves or coupled to a solid phase support and be used to remove inhibitor antibodies to Factor VIII from blood directly in human patients or from blood or blood plasma by immunoabsorption in an extra-corporeal circulation system. When fragments are administered to a human patient, they are preferably administered by intravenous injection.

I claim:

1. A cDNA consisting essentially of the complete coding sequence for a fragment of Factor VIIIC selected from the group consisting of a polypeptide in glycosylated or unglycosylated form extending from about amino acid 1563 to about amino acid 2332 of human Factor VIIIC and having an unglycosylated $M_r$ value of about 88,000 d as determined by SDS-PAGE, a polypeptide in glycosylated or unglycosylated form extending from about amino acid 326 to about amino acid 742 of human Factor VIIIC and having an unglycosylated $M_r$ value of about 49,000 d as determined by SDS-PAGE, a polypeptide in glycosylated or unglycosylated form extending from about amino acid 1974 to about amino acid residue 2332 of human Factor VIIIC and having an unglycosylated $M_r$ of about 37,500 d as determined by SDS-PAGE and a polypeptide in glycosylated or unglycosylated form extending from about amino acid residue 2052 to about amino acid residue 2332 of human Factor VIIIC.

2. A self-replicating expression vector capable of expressing in an in vitro culture system a recombinant Factor VIIIC fragment selected from the group consisting of a polypeptide in glycosylated or unglycosylated form extending from about amino acid 1563 to about amino acid 2332 of human Factor VIIIC and having an unglycosylated $M_r$ value of about 88,000 d as determined by SDS-PAGE, a polypeptide in glycosylated or unglycosylated form extending from about amino acid 326 to about amino acid 742 of human Factor VIIIC and having an unglycosylated $M_r$ value of about 49,000 d as determined by SDS-PAGE, a polypeptide in glycosylated or unglycosylated form extending from about amino acid 1974 to about amino acid residue 2332 of human Factor VIIIC and having an unglycosylated $M_r$ of about 37,500 d as determined by SDS-PAGE and a polypeptide in glycosylated or unglycosylated form extending from about amino acid residue 2052 to about amino acid residue 2332 of human Factor VIIIC.

3. A plasmid having the ATCC designation 67090 or 67091.

4. A cDNA consisting essentially of the complete coding sequence for a fragment of Factor VIIIC wherein the fragment is a polypeptide in glycosylated or unglycosylated form extending from about amino acid 1563 to about amino acid 2332 of human Factor VIIC and having an unglycosylated $M_r$ value of about 88,000 d as determined by SDS-PAGE.

5. A cDNA consisting essentially of the complete coding sequence for a fragment of Factor VIIIC wherein the fragment is a polypeptide in glycosylated or unglycosylated form extending from about amino acid 326 to about amino acid 742 of human Factor VIIIC and having an unglycosylated $M_r$ value of about 49,000 d as determined by SDS-PAGE.

6. A cDNA consisting essentially of the complete coding sequence for a fragment of Factor VIIIC wherein the fragment is a polypeptide in glycosylated or unglycosylated form extending from about amino acid 1974 to about amino acid 2332 of human Factor VIIIC and having an unglycosylated $M_r$ value of about 37,500 d as determined by SDS-PAGE.

7. A cDNA consisting essentially of the complete coding sequence for a fragment of Factor VIIIC wherein the fragment is a polypeptide in glycosylated or unglycosylated form extending from about amino acid 2052 to about amino acid 2332 of human Factor VIIIC.

8. A self-replicating expression vector capable of expressing in an in vitro culture system a recombinant Factor VIIIC fragment wherein the fragment is a polypeptide in glycosylated or unglycosylated form extending from about amino acid 1563 to about amino acid 2332 of human Factor VIIIC and having an unglycosylated $M_r$ value of about 88,000 d as determined by SDS-PAGE.

9. A self-replicating expression vector capable of expressing in an in vitro culture system a recombinant Factor VIIIC fragment wherein the fragment is a polypeptide in glycosylated or unglycosylated form extending from about amino acid 326 to about amino acid 742 of human Factor VIIIC and having an unglycosylated $M_r$ value of about 49,000 d as determined by SDS-PAGE.

10. A self-replicating expression vector capable of expressing in an in vitro culture system a recombinant Factor VIIIC fragment wherein the fragment is a polypeptide in glycosylated or unglycosylated form extending from about amino acid 1974 to about amino acid 2332 of human Factor VIIIC and having an unglycosylated $M_r$ value of about 37,500 d as determined by SDS-PAGE.

11. A self-replicating expression vector capable of expressing in an in vitro culture system a recombinant Factor VIIIC fragment wherein the fragment is a polypeptide in glycosylated or unglycosylated form extending from about amino acid 2052 to about amino acid 2332 of human Factor VIIIC.

12. A method for producing a fragment of Factor VIIIC selected from the group consisting of a polypeptide in glycosylated or unglycosylated form extending from about amino acid 1563 to about amino acid 2332 of human Factor VIIIC and having an unglycosylated $M_r$ value of about 88,000 d as determined by SDS-PAGE, a polypeptide in glycosylated or unglycosylated form extending from about amino acid 326 to about amino acid 742 of human Factor VIIIC and having an unglycosylated $M_r$ value of about 49,000 d as determined by SDS-PAGE, a polypeptide in glycosylated or unglycosylated form extending from about amino acid 1974 to about amino acid 2332 of human Factor VIIIC and having an unglycosylated $M_r$ of about 37,500 d as determined by SDS-PAGE and a polypeptide in glycosylated or unglycosylated form extending from about amino acid 2052 to about amino acid 2332 of human Factor VIIIC comprising:

preparing a replicable expression vector capable of expressing a DNA sequence encoding said Factor VIIIC fragment in a suitable host cell;

transforming said host cell with said vector;

maintaining said recombinant host system under conditions permitting expression of said Factor VIIIC fragment-encoding DNA sequence to produce Factor VIIIC fragment protein; and recovering said Factor VIIIC fragment protein.

13. The method of claim 12, wherein said Factor VIIIC fragment protein is recovered by reacting the proteins expressed by the recombinant host system with at least one composition comprising a compound which binds specifically to said Factor VIIIC fragment protein.

* * * * *

UNITED STATES PATENT AND TRADEMARK OFFICE
CERTIFICATE OF CORRECTION

PATENT NO. : 5,149,637
DATED : September 22, 1992
INVENTOR(S) : D. H. Scandella et al.

It is certified that error appears in the above-identified patent and that said Letters Patent is hereby corrected as shown below:

Column 1, line 6, after "4,980,456" insert --This invention was made with government support under HL 31950 and HL 35090, awarded by the National Institutes of Health. The government has certain rights in the invention.--

Signed and Sealed this

Fourth Day of January, 1994

Attest:

BRUCE LEHMAN

*Attesting Officer*   *Commissioner of Patents and Trademarks*